United States Patent [19]

Gebhardt et al.

[11] Patent Number: 4,482,554

[45] Date of Patent: Nov. 13, 1984

[54] PHARMACEUTICAL COMPOSITIONS CONTAINING OXICAM DERIVATIVES AND PROCESS FOR THEIR PREPARATION

[75] Inventors: Uwe Gebhardt; Helmut Augart, both of Waldkirch; Adolf Knecht, Freiburg, all of Fed. Rep. of Germany

[73] Assignee: Warner-Lambert Company, Morris Plains, N.J.

[21] Appl. No.: 488,922

[22] Filed: Apr. 27, 1983

[30] Foreign Application Priority Data

May 8, 1982 [DE] Fed. Rep. of Germany ....... 3217315

[51] Int. Cl.$^3$ ............................................. A61K 31/54
[52] U.S. Cl. .................................................... 424/246
[58] Field of Search ........................................ 424/246

[56] References Cited

U.S. PATENT DOCUMENTS 4,233,299 11/1980 Trummlitz et al. ................ 424/246

OTHER PUBLICATIONS

Chem. Abst, 88-121216a, (1978).
Rheumatheropie, 3, 22, (1981).

*Primary Examiner*—Stanley J. Friedman
*Attorney, Agent, or Firm*—Ronald A. Daignault

[57] ABSTRACT

The present invention provides a pharmaceutical composition containing at least one oxicam derivative of the general formula:

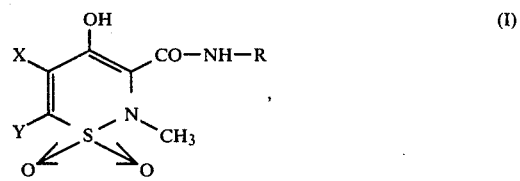

in which R is a heterocyclic ring and X together with Y represent a condensed aromatic ring, together with a more than equimolar amount of an organic base of the general formula:

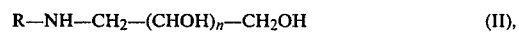

$$R-NH-CH_2-(CHOH)_n-CH_2OH \qquad (II),$$

in which R is a hydrogen atom or an alkyl radical containing up to 6 carbon atoms and n is 3 or 4.

8 Claims, No Drawings

PHARMACEUTICAL COMPOSITIONS CONTAINING OXICAM DERIVATIVES AND PROCESS FOR THEIR PREPARATION

The present invention is concerned with pharmaceutical compositions containing oxicam derivatives and with the preparation thereof.

Oxicam derivatives of the general formula:

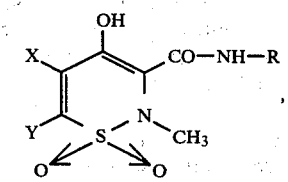

in which R is a heterocyclic ring, for example a pyridine or 5-methyl-3-isoxazole ring, and X together with Y represent a condensed aromatic ring, for example a benzene or thiophene ring, are so poorly soluble not only in water but also in physiologically acceptable organic solvents and in mixtures thereof that highly concentrated pharmaceutical compositions, especially injection solutions, have hitherto not been commercially available. Those with a sufficient content of active material could hitherto also not be prepared.

Oxicam derivatives of general formula (I), for example piroxicam (R=pyridyl X, Y=a benzene ring) or isoxicam (R=5-methyl-3-isoxazolyl X,Y=a benzene ring) are highly effective substances with an antiinflammatory action which hitherto have only been administered orally. Further substances in which X,Y represent a thiophene ring have also been described (see Rheumatherapie, 3, 22/1981). Sudoxicam, which is also a known substance has been described in C.A. 88 (17) 1212/6 a.

Since it is known of agents with a similar or identical activity that, especially in the case of inflammatory and painful diseases of the limbs, a local administration by injection can be considerably more quickly effective than a peroral, systemic treatment, there is a great need for highly concentrated, injectable compositions containing active materials of the oxicam type. This applies especially for intra-articular administration, which was hitherto not possible in the case of the non-steroidal agents.

European Patent Specification No. 2482 admittedly describes attempts to increase the solubility of oxicam derivatives by salt formation with equimolar amounts of N-methyl-D-glucamine. However, this only enables a slight improvement of the solubility to be achieved.

Our own attempts to solve the problem have also shown that the solubility of compounds of the oxicam type of general formula (I) in water can admittedly be improved by a stoichiometric salt formation with bases on the phenolic hydroxyl group in the 4-position but the solubility of these salts is insufficient for the production of concentrated solutions so that, in this way, the necessary minimisation of the volume of administration could not be achieved.

Especially in the case of oxicam derivatives of general formula (I), there is, in addition, the serious problem of instability of their solutions. Even when such compounds or the salts thereof have been brought into solution, these show a strong tendency, even after a relatively short time, to deposit particles and again to precipitate out a part of the active material. For injection solutions, this is naturally not acceptable.

Thus, the sodium salts of isoxicam show, shortly after their preparation, a solubility in water of about 24 mg/ml which, however, in the course of 4 months, decreases by precipitation from the solution to about 5 to 6 mg/ml. In the case of potassium salts, the initial solubility in water is about 30 mg/ml but this decreases within the course of 4 months to 20 mg/ml.

With methylglucamine, stoichiometric salts of isoxicam are obtained which contain 49 mg of active material per milliliter of solution but these are also unstable and again precipitate out considerable amounts of active material. A curious thing is hereby the discovery that the degree of precipitation of active material from the salt solution is, over wide ranges, not dependent upon the concentration so that such solutions are also not suitable for parenteral administration, even in low concentrations.

Attempts to increase the solubility of such stoichiometric salts by the addition of physiologically acceptable organic solvents were also unsuccessful since, on the one hand, the solubility is hereby only slightly increased and, on the other hand, subsequent precipitations of the active material from the solutions formed are thereby not prevented.

It is an object of the present invention to provide highly concentrated and stable solutions of active materials as well as lyophilisates of the oxicam type, especially of isoxicam, which make possible an effective parenteral and local treatment of inflammatory diseases.

We have now found that compounds of the general formula (I) can, surprisingly, be converted into relatively highly concentrated solutions which are stable for several months when the stoichiometric proportion of base of 1:1, which is known for the production of organic salts, is increased and simultaneously a physiologically acceptable organic, water-miscible solvent is added in a concentration of about 5 to 70 volume % and preferably of 10 to 30 volume %. The proportion of base is preferably increased to a proportion of 1:1.1 to 1:2.5, the most favourable range being from 1:1.2 to 1:2.

There are thereby unexpectedly obtained, which was not to have been foreseen by the expert, highly concentrated solutions with a content of up to 30% and preferably of 10 to 20%, referred to the amount of active material used, which, even after storage for 15 months, display no deposition of active material. It is most surprising that this stability is fully retained even at low temperatures.

Due to the preponderance of the basic component, the pH value of the solutions obtained increases to 9 to 10, depending upon the ratio of the components. In spite of this pH value, which is relatively high for parenteral administration, as animal experiments have shown, such solutions, in the case of intramuscular, intraarterial and intravenous administration and especially also in the case of intraarticular administration, are outstandingly compatible and do not give rise to any tissue irritation. Since the viscosity of the solutions of 5 to 20 mPa.s (Millipasqual.seconds) is rather high, from this point of view a certain degree of incompatibility was to have been expected. However, this has not been confirmed, even in the case of high concentrations. In spite of this surprising finding, the proportion of base should not be too high since, in the case of pH values in the non-physiological range of over 10, tissue irritation and tissue damage might be expected.

Especially suitable organic bases are those of general formula II $$R-NH-CH_2-(CHOH)_n-CH_2OH \quad (II),$$

wherein R is a hydrogen atom or an alkyl group containing 1 to 6 carbon atoms and n is 3 or 4.

Preferred are compounds of formula II wherein R is alkyl containing 1 to 3 carbon atoms. Representative compounds of formula II are for example the following sugar-alcoholes: D-glucamin, N-methyl-D-glucamin, N-hexyl-D-glucamin, N-butyl-D-glucamin, N-methyl-D-mannamin, N-ethyl-D-galactamin, N-methyl-DL-arabin-amin and N-methyl-L-rhamnamin, N-methyl-D-xylamin and N-butyl-D-xylamin.

The preparations according to the present invention should show an as low as possible viscosity. This is the reason, why compounds with a low molecular weight with R=methyl and n=3 or 4 are preferred for the manufacture of injection solutions.

Methyl-glucamin (R=methyl, n=4) is known as a physiologically harmless compound and has hitherto been widely used in pharmaceutical preparations (e.g. x-ray contrast media). Furthermore it is readily available on the market. Due to its low viscosity methyl-glucamine is for the time being the most favorable compound of formula II.

It is self-evident that the base used according to the present invention must be freely available so that the proportion of base, in the case of the addition of acids to the solution, must naturally be correspondingly increased.

As organic solvents there can be used all those which are miscible with water and which can also be used without restriction for parenteral administration, for example propylene glycol, polyethylene glycol and liquid acid amides, such as dimethyl formamide and dimethyl acetamide. Especially preferred are the polyethylene glycols with the designations PEG 200, PEG 300 and PEG 400, as well as dimethyl acetamide. The symbol PEG 200/300/400 etc. means that the used polyethylene glycoles have a nominal average molecular weight (according USP) of the given number.

The solutions are prepared by heating the desired amount of active material together with the excess of base according to the present invention and the organic solvent to about 40° to 80° C. and preferably to 60° to 70° C. and subsequently worked up in known manner to give sterile solutions.

Of course, the solutions according to the present invention can be used not only for pharmaceutical compositions for parenteral administration but also for the preparation of salves, gels, ophthalmological compositions, drops and syrups.

They can also be further worked up to give lyophilisates. In this case, the organic solvent is dispensable since lyophilized products are dissolved only shortly before their use in an appropriate solvent, e.g. water. The highly concentrated solutions are then applied within not more than 60 minutes. Thus an increased stability of the solution is not necessary. However, for the preparation of the lyophilized preparations, the proportion of base should not go below 1.35 mole and should not substantially exceed about 2 mole. For injection solutions, the most favourable proportion of base is from 1.2 to about 2 mole.

If, in the case of highly viscous solutions according to the present invention, it is desired to lower the viscosity for the parenteral administration, then, immediately before the administration, the desired amount of water can readily be added without the possibility of a precipitation of the active material.

The preparation of the lyophilisates is preferably carried out by dissolving the active material, together with 1.5 to 2 mole of base, in a sufficient amount of water at a temperature of from 40° to 80° C. The clear solution is filtered through a membrane filter of 0.22 μm and placed into small glass vessels, rapidly frozen and then lyophilized. After the addition of an appropriate amount of water, the lyophilized solid material dissolves immediately and gives, even in the absence of an organic solvent, a clear solution which is stable for at least 30 minutes.

Consequently, according to the present invention, there are provided pharmaceutical compositions containing at least one oxicam derivative of general formula (I) and a more than equimolar amount of an organic base of general formula (II), referred to the oxicam derivative.

The present invention also provides aqueous solutions containing at least one oxicam derivative of general formula (I), together with a more than equimolar amount of a base of general formula (II) and an amount of 5 to 70 volume % of a physiologically compatible, water-miscible organic solvent.

Furthermore, the present invention provides a process for the preparation of a pharmaceutical composition containing at least one oxicam derivative of general formula (I), wherein the active material, together with more than 1 mole of an organic base of general formula (II), are dissolved in an aqueous solution with a proportion of 5 to 70% of a physiologically compatible, water-miscible organic solvent at a temperature of about 40° to 80° C.

The present invention also provides a process for the preparation of a pharmaceutical composition containing at least one oxicam derivative of general formula (I), wherein the active material is dissolved, together with a more than equimolar amount of an organic base of general formula (II), at 40° to 80° C. in an amount of water sufficient for complete dissolving and the solution obtained, after distribution into small storage vessels, is rapidly frozen in known manner and lyophilised.

The following examples are given for the purpose of illustrating the present invention:

EXAMPLE 1

(a) 10.75 g methyl-glucamine (I) are dissolved in 30 g distilled water. Into this solution are successively added 15 g isoxicam (II) and 30 g polyethylene glycol (III) (PEG 200). The mixture is warmed up to 60°–70° C. until dissolving is complete. After cooling, the solution is made up to 100 ml with distilled water and subsequently filtered through a 0.22 μm membrane filter. The clear solution thus obtained is placed into 1 ml ampoules, each of which contains 150 mg isoxicam.

The following solutions are prepared in an analogous manner:

| | |
|---|---|
| (b) methyl-glucamine (I) | 10.75 g |
| isoxicam (II) | 15.0 g |
| PEG 200 (III) | 20.0 g |
| (c) methyl-glucamine (I) | 10.75 g |
| isoxicam (II) | 15.0 g |
| PEG 200 (III) | 10.0 g |
| (d) methyl-glucamine (I) | 10.75 g |

|   |   |   |
|---|---|---|
| | isoxicam (II) | 15.0 g |
| | PEG 300 (III) | 20.0 g |
| (e) | methyl-glucamine (I) | 10.75 g |
| | isoxicam (II) | 15.0 g |
| | PEG 400 (III) | 10.0 g |
| (f) | methyl-glucamine (I) | 10.75 g |
| | isoxicam (II) | 15.0 g |
| | dimethylacetamide (III) | 30.0 g |
| (g) | methyl-glucamine (I) | 10.75 g |
| | piroxicam (II) | 15.0 g |
| | PEG 200 (III) | 30.0 g |
| (h) | methyl-glucamine (I) | 10.75 g |
| | piroxicam (II) | 15.0 g |
| | dimethylacetamide (III) | 30.0 g |

The examples (i) to (n) are made up to 50 ml:

|   |   |   |
|---|---|---|
| (i) | ethylglucamine (I) | 5.76 g |
| | isoxicam (II) | 7.50 g |
| | PEG 200 (III) | 15.00 g |
| (j) | ethylglucamine (I) | 6.08 g |
| | isoxicam (II) | 7.50 g |
| | PEG 200 (III) | 15.00 g |
| (k) | ethylglucamine (I) | 7.02 g |
| | isoxicam (II) | 7.50 g |
| | PEG 200 (III) | 15.00 g |
| (l) | ethylglucamine (I) | 9.36 g |
| | isoxicam (II) | 7.5 g |
| | PEG 200 (III) | 15.00 g |
| (m) | methyl-glucamine (I) | 5.38 g |
| | Sudoxicam | 7.5 g |
| | PEG 200 (III) | 15.0 g |
| (n) | ethylglucamine (I) | 5.36 g |
| | piroxicam (II) | 7.5 g |
| | PEG 200 (III) | 15.0 g |
| (o) | ethylglucamine (I) | 5.76 g |
| | isoxicam (II) | 7.5 g |
| | dimethylacetadine (III) | 15.0 g |
| (p) | ethylglucamine (I) | 5.76 g |
| | isoxicam (II) | 7.5 g |
| | PEG 400 (III) | 15.0 g |
| (q) | ethylglucamine (I) | 5.76 g |
| | isoxicam (II) | 7.5 g |
| | PEG 300 (III) | 15.0 g |
| (n) | n-propylglucamine (I) | 6.0 g |
| | isoxicam (II) | 7.5 g |
| | PEG 200 (III) | 15.0 g |

EXAMPLE 2

10.75 g methyl-glucamine are dissolved in 20 g distilled water. After the addition of 15 g isoxicam, the solution is made up to 100 ml with PEG 200. The mixture is warmed to 40° C. until dissolving is complete, then cooled, filtered through a 0.22 μm filter and filled into 1 ml ampoules. In an analogous manner there is obtained a solution by using the following components:

Ethylglucamine: 11.29 g
Isoxicam: 15.0 g
PEG 200: q.s. 100 ml

EXAMPLE 3

13.1 g methyl-glucamine are dissolved in 50 ml distilled water and the solution, after the addition of 15.0 g isoxicam, made up to 100 ml. While stirring, the mixture is heated to 80° C. until dissolving is complete. After cooling to 30° to 40° C., the solution is filtered through a 0.22 μm membrane filter, portions of 1 ml of the solution are placed into glass lyophilisation vessels and frozen at −40° to −50° C. and subsequently lyophilized. By the addition of 1 ml water, an injection solution can be prepared from the lyophilisate which remains clear and free of particles for at least 30 minutes. In an analogous manner there are obtained lyophilisates by using the following components

|   |   |   |
|---|---|---|
| (b) | ethylglucamine | 13.1 g |
| | isoxicam | 15.0 g |
| (c) | ethylglucamine | 14.04 g |
| | isoxicam | 15.0 g |

EXAMPLE 4

In a first stage 528.5 g of methylglucamine are dissolved in 2,000 g water while stirring. This solution is then mixed with a mixture of 667.5 g polyethylene glycol 200 and 1.136.5 g water. The mixture thus obtained is then warmed to 70° C. and mixed with 667.5 g isoxicam. Once the active substance has dissolved the mixture is allowed to cool to ambient temperature while stirring and is filtered.

77 g of carbomer (USP 20/NF XV=distributed in Germany as Carbopol 940 ®) are suspended in a second batch and dispersed in a non-agglutinated state. To this dispersion is added a solution of 238.7 g methylglucamine in 600 g water and stirred until an almost clear gel has formed.

The two batches are then combined and stirred homogeneously until a clear gel is obtained.

We claim:

1. A pharmaceutical composition comprising an aqueous solution containing at least one oxicam derivative of the general formula:

$$\begin{array}{c} \text{OH} \\ \text{X} \diagdown \diagup \text{CO—NH—R} \\ \text{Y} \diagdown \diagup \text{N} \diagdown \text{CH}_3 \\ \text{O}^{\diagup \text{S}} \diagdown \text{O} \end{array}$$

in which R is a pyridine or 5-methyl-3-isoxazole ring and X together with Y represent a condensed aromatic ring, together with 1.2 to 2 moles per mole of oxicam derivative of a base of general formula:

$$R-NH-CH_2-(CHOH)_n-CH_2OH$$

in which R is a hydrogen atom or an alkyl radical containing up to 6 carbon atoms and n is 3 or 4.

2. A pharmaceutical composition according to claim 1 wherein the oxicam derivative is isoxicam.

3. A pharmaceutical composition according to claim 1 wherein the base is methyl-glucamine.

4. A pharmaceutical composition according to claim 1 wherein the aqueous solution further contains a proportion of 5–70 volume % of a physiologically compatible, water-miscible organic solvent.

5. A pharmaceutical composition according to claim 4, wherein the water-miscible organic solvent is polyethylene glycol or dimethylacetamide.

6. A pharmaceutical composition according to claim 1, wherein the concentration of the oxicam derivative is from 10–20%.

7. A pharmaceutical composition according to claim 4, wherein the proportion of organic solvent is from 10–30% by weight.

8. A pharmaceutical composition in lyophilized form containing at least one oxicam derivative of the general formula:

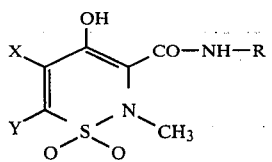
in which R is a pyridine or 5-methyl-3-isoxazole ring and X together with Y represent a condensed aromatic ring, together with 1.35-2 moles per mole of oxicam derivative of a base of the general formula:
$$R-NH-CH_2-(CHOH)_n-CH_2OH \qquad (II)$$
in which R is a hydrogen atom or an alkyl radical containing up to six carbon atoms and n is 3 or 4.
* * * * *